(12) United States Patent
Belt et al.

(10) Patent No.: US 11,026,656 B2
(45) Date of Patent: Jun. 8, 2021

(54) ULTRASOUND DATA VISUALIZATION APPARATUS

(71) Applicant: KONINKLIJKE PHILIPS N.V., Eindhoven (NL)

(72) Inventors: Harm Jan Willem Belt, Weert (NL); Godefridus Antonius Harks, Rijen (NL); Steven Antonie Willem Fokkenrood, s-Hertogenbosch (NL); Monica Tavanti, Eindhoven (NL); Alexander Franciscus Kolen, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1549 days.

(21) Appl. No.: 14/432,583

(22) PCT Filed: Sep. 12, 2013

(86) PCT No.: PCT/IB2013/058474
§ 371 (c)(1),
(2) Date: Mar. 31, 2015

(87) PCT Pub. No.: WO2014/060870
PCT Pub. Date: Apr. 24, 2014

(65) Prior Publication Data
US 2015/0265241 A1 Sep. 24, 2015

Related U.S. Application Data

(60) Provisional application No. 61/715,369, filed on Oct. 18, 2012.

(51) Int. Cl.
*A61B 8/08* (2006.01)
*G06T 7/00* (2017.01)
(Continued)

(52) U.S. Cl.
CPC .......... *A61B 8/0841* (2013.01); *A61B 8/0833* (2013.01); *A61B 8/0883* (2013.01);
(Continued)

(58) Field of Classification Search
CPC ... A61B 8/5276; A61B 8/0858; A61B 8/0883; A61B 8/12; A61B 8/463; A61B 8/465; A61B 8/486; A61B 8/5284
See application file for complete search history.

(56) References Cited

U.S. PATENT DOCUMENTS 5,785,654 A * 7/1998 Iinuma ............... G01S 7/52085
600/441
5,873,830 A 2/1999 Hossack
(Continued)

FOREIGN PATENT DOCUMENTS

JP H04146739 A 5/1992
JP 08252253 A 10/1996
(Continued)

OTHER PUBLICATIONS

Vakoc et al., "Real-time microscopic visualization of tissue response to laser thermal therapy" Journal of Biomedical Optics vol. 12 (2) Mar./Apr. 2007, p. 020501-1-020501-3.*
(Continued)

*Primary Examiner* — Katherine L Fernandez
*Assistant Examiner* — Colin T. Sakamoto

(57) ABSTRACT

The invention relates to an ultrasound data visualization apparatus for visualizing ultrasound data showing an object during an interventional procedure. A reference image (65) and a current image (68) of the object are simultaneously displayed, wherein the current image corresponds to a current time interval and the reference image corresponds to a reference time interval and wherein the current time interval and the reference time interval correspond to dif-
(Continued)

ferent phases of the interventional procedure. The current image can be shown therefore with, for instance, a relatively high temporal resolution for allowing a user to observe detailed object changes, which may be caused by the interventional procedure, while an overview over different phases of the interventional procedure can still be provided, because also the reference image is displayed and can be used by a user for comparing the current image with the reference image.

19 Claims, 8 Drawing Sheets

(51) Int. Cl.
    *A61B 8/00*     (2006.01)
    *A61B 18/14*     (2006.01)
    *A61B 8/12*     (2006.01)

(52) U.S. Cl.
    CPC .............. *A61B 8/445* (2013.01); *A61B 8/463* (2013.01); *A61B 8/467* (2013.01); *A61B 8/486* (2013.01); *A61B 8/5207* (2013.01); *A61B 8/5238* (2013.01); *A61B 18/1492* (2013.01); *G06T 7/0016* (2013.01); *A61B 8/12* (2013.01); *A61B 8/5284* (2013.01); *A61B 8/543* (2013.01)

(56) References Cited

U.S. PATENT DOCUMENTS

| | | | |
|---|---|---|---|
| 7,022,075 B2* | 4/2006 | Grunwald | A61B 8/00 600/446 |
| 7,606,402 B2* | 10/2009 | Heimdal | A61B 8/00 382/128 |
| 8,265,358 B2 | 9/2012 | Abe | |
| 8,774,906 B2 | 7/2014 | Harks et al. | |
| 2002/0035329 A1 | 3/2002 | Kamiyama | |
| 2003/0045795 A1 | 3/2003 | Bjaerum | |
| 2003/0045796 A1 | 3/2003 | Friedman | |
| 2007/0055158 A1 | 3/2007 | Jackson et al. | |
| 2008/0304730 A1 | 12/2008 | Vasuhiko | |
| 2009/0112132 A1* | 4/2009 | Chang | A61B 5/416 601/3 |
| 2009/0306511 A1 | 12/2009 | Yamagata | |
| 2010/0145197 A1 | 6/2010 | Stapf et al. | |
| 2010/0160781 A1* | 6/2010 | Carter | A61B 8/06 600/439 |
| 2012/0000454 A1 | 1/2012 | Kraus | |
| 2012/0143055 A1 | 6/2012 | Ng et al. | |
| 2012/0232388 A1* | 9/2012 | Curra | A61B 8/466 600/438 |
| 2012/0310089 A1* | 12/2012 | Miyachi | A61B 8/0858 600/440 |
| 2013/0158537 A1 | 6/2013 | Deladi et al. | |

FOREIGN PATENT DOCUMENTS

| | | |
|---|---|---|
| JP | 2007014605 A | 1/2007 |
| JP | 2009285478 A | 12/2009 |
| WO | 2010082146 A1 | 7/2010 |
| WO | 2011158136 A1 | 12/2011 |
| WO | 2013140358 A1 | 9/2013 |

OTHER PUBLICATIONS

123sonography, "M-Mode Measurements of the Left Ventricle". Youtube video, Jun. 21, 2010 https://www.youtube.com/watch?v=WJ6EfMZwr6o (Year: 2010).*

Wright, M. et al., "Real-time lesion assessment using a novel combined ultrasound and radiofrequency ablation catheter". Heart Rhythm Society, vol. 8, No. 2, pp. 304-312, Feb. 2011.

* cited by examiner

ULTRASOUND DATA VISUALIZATION APPARATUS

CROSS-REFERENCE TO PRIOR APPLICATIONS

This application is the U.S. National Phase application under 35 U.S.C. § 371 of International Application Serial No. PCT/IB2013/058474, filed on Sep. 12, 2013, which claims the benefit of U.S. Application Ser. No. 61/715,369, filed on Oct. 18, 2012. These applications are hereby incorporated by reference herein.

FIELD OF THE INVENTION

The invention relates to an ultrasound data visualization apparatus, an ultrasound data visualization method and an ultrasound data visualization computer program for visualizing ultrasound data showing an object during an interventional procedure. The invention relates further to an interventional apparatus comprising the ultrasound data visualization apparatus.

BACKGROUND OF THE INVENTION

In cardiac ablation procedures an ablation catheter is introduced into a heart of a living being, wherein the tip of the ablation catheter comprises, for instance, an ablation electrode for applying radio frequency energy to cardiac tissue to be ablated. Moreover, the tip of the ablation catheter can comprise an ultrasound transducer for ultrasonically monitoring the ablation procedure.

In order to provide an overview over the entire ablation procedure on a display, the temporal resolution of the ultrasound data shown on the display is relatively low, thereby making it relatively hard for a physician to ultrasonically monitor detailed tissue changes caused by the ablation procedure.

SUMMARY OF THE INVENTION

It is an object of the present invention to provide an ultrasound data visualization apparatus, an ultrasound data visualization method and an ultrasound data visualization computer program for visualizing ultrasound data showing an object during an interventional procedure, which allows for an improved monitoring of the interventional procedure. It is a further object of the present invention to provide an interventional apparatus comprising the ultrasonically data visualization apparatus.

In a first aspect of the present invention an ultrasound data visualization apparatus for visualizing ultrasound data showing an object during an interventional procedure is presented, wherein the ultrasound data visualization apparatus comprises:
  an ultrasound image providing unit for providing a temporally dependent ultrasound image of the object,
  a current image determining unit for determining a current image of the object based on a part of the temporally dependent ultrasound image, which corresponds to a current time interval,
  a reference image determining unit for determining a reference image of the object based on a part of the temporally dependent ultrasound image, which corresponds to a reference time interval, wherein the reference time interval and the current time interval correspond to different phases of the interventional procedure,
  a display for simultaneously displaying the reference image and the current image.

Since the display simultaneously displays the reference image and the current image, wherein the current image corresponds to a current time interval and the reference image corresponds to a reference time interval and wherein the current time interval and the reference time interval correspond to different phases of the interventional procedure, the current image can be shown with a relatively high temporal resolution, wherein an overview over different phases of the interventional procedure can still be provided, because also the reference image is displayed and can be used by the physician for comparing the current image with the reference image. Thus, the physician can observe detailed object changes, which may be caused by the interventional procedure, wherein the physician can still have an overview over different phases of the interventional procedure.

The ultrasound image providing unit and the current image determining unit are preferentially adapted to continuously update the current image, in particular, in a wrapping fashion similar to the updating of M-mode images, whereas the reference image may be a constant image.

In an embodiment the interventional procedure includes an object-influence phase during which the object is influenced at a location on the object by applying energy to the object by using an energy application element, a pre-object-influence phase and a post-object-influence phase, wherein the reference time interval and the current time interval correspond to different of these phases. For instance, the interventional procedure can be an ablation procedure for ablating the object, wherein the reference time interval can correspond to a pre-object-influence phase being a pre-ablation phase and the current time interval can correspond to the object-influence phase during which ablation energy is applied to the object or wherein the reference time interval can correspond to the object-influence phase and the current time interval can correspond to the post-object-influence phase being, in this example, a post-ablation phase in which the ablation procedure has been completed. Thus, the ultrasound data visualization apparatus can be used to observe details in changes of the object during an ablation procedure, wherein still an overview over different phases of the ablation procedure can be provided. The ablation procedure is preferentially a cardiac ablation procedure for ablating cardiac tissue.

The ultrasound data visualization apparatus can comprise an energy application time providing unit for providing a start time at which the object-influence phase starts, wherein the reference image determining unit is adapted to determine the reference time interval depending on the provided start time and to determine the reference image based on the part of the temporally dependent ultrasound image, which corresponds to the determined reference time interval. In particular, the reference image determining unit can be adapted to determine the reference time interval as a time interval immediately before the provided start time. An image can therefore be provided as a reference image, which corresponds to the last part of the pre-object-influence phase.

The energy application time providing unit can also be adapted to provide an end time at which the object-influence phase ends, wherein the reference image determining unit can be adapted to determine the reference time interval depending on the provided end time and to determine the reference image based on the part of the temporally dependent ultrasound image, which corresponds to the determined reference time interval. In particular, the ultrasound image providing unit can be adapted to determine the reference time interval as a time interval immediately before the provided end time. The reference time interval can therefore correspond to the last part of the object-influence phase.

Thus, the reference time interval can be automatically determined based on the process of applying energy to the object, wherein, for instance, the reference time interval and, thus, the reference image can be automatically updated based on the actual energy application procedure.

In an embodiment, during the interventional procedure the energy application element is moved to different locations on the object for influencing the object at the different locations, wherein the ultrasound data visualization apparatus further comprises a location change signal providing unit for providing a location change signal indicating when the energy application element has reached a new location at which the object is to be influenced, wherein the reference image determining unit is adapted to determine the time interval immediately after the energy application element has reached the new location as the reference time interval in the pre-object-influence phase depending on the provided location change signal and to determine the reference image based on the part of the temporally dependent ultrasound image, which corresponds to the determined reference time interval. Thus, each time the energy application element has been moved to a new location, at which the object should be influenced, the reference image can be updated such that the reference image corresponds to the actual location on the object. The location change signal providing unit can comprise, for instance, a push button, which may be arranged on a hand grip of the energy application element, which may be an ablation catheter, wherein the push button can be pushed, if the energy is applied, and wherein the location change signal can be provided depending on whether the push button is pushed. The location change signal providing unit can also be adapted to automatically determine the location change signal from the provided temporarily dependent ultrasound image.

The ultrasound data visualization apparatus may comprise an input device for allowing a user to input the reference time interval, wherein the reference image determining unit may be adapted to determine the reference image based on the part of the temporally dependent ultrasound image, which corresponds to the determined reference time interval. This allows a user like a physician to adapt the reference image as desired.

The ultrasound data visualization apparatus can further comprise a physiological signal providing unit for providing a temporally dependent physiological signal corresponding to the reference and current time intervals, wherein the current image determining unit and the reference image determining unit are adapted to determine temporally dependent current and reference images, wherein the display is adapted to simultaneously display the provided physiological signal and the current and reference images, wherein the provided physiological signal and the current and reference images are temporally aligned on the display. The physiological signal is preferentially an electrocardiography signal. Displaying the physiological signal and the current and reference images temporarily aligned allows the user to grasp characteristics of the object shown in the images and the physiological properties represented by the physiological signal in different phases of the interventional procedure very easily by just looking on the display.

The ultrasound image providing unit and the current image determining unit are preferentially adapted to provide the current image in realtime. The current image data are therefore shown to the user very fast such that the user can immediately react on the characteristics of the object shown in the current image.

The current time interval and the reference time interval are preferentially smaller than the temporal distance between the current time interval and the reference time interval. For instance, if the object is cardiac tissue, the reference time interval can be about two seconds and the current time interval can be also about two seconds or some seconds larger, whereas the temporal distance between the reference time interval and the current time interval can be one or several minutes.

Preferentially, the reference image and the current image are shown with the same temporal resolution. This allows for an easy comparison between details of the object in the current image and in the reference image.

In an embodiment the current image determining unit is adapted to determine the current image as a part of the provided temporally dependent ultrasound image or of a processed image obtained by processing the provided temporally dependent ultrasound image, which corresponds to the current time interval, as the current image, wherein the reference image determining unit is adapted to determine the reference image as a part of the provided temporally dependent ultrasound image or of the processed image, which corresponds to the reference time interval, as the reference image. The processed image is preferentially i) a motion image, ii) a strain image, iii) a gated image, if the object is a repetitively moving object, or iv) a likelihood image indicating the likelihood that a certain image element represents a certain part of the object. In particular, the ultrasound data visualization apparatus can comprise a repetitive signal providing unit for providing a repetitive signal being indicative of a repetitive movement of the object, wherein the current image determining unit and the reference image determining unit can be adapted to provide gated reference and current images for the reference and current time intervals, respectively, based on the provided repetitive signal and the provided temporally dependent ultrasound image. The gated images can be static gated images or dynamic gated images. This can allow for a comparison of characteristics of the object in the current image and in the reference image, which may not be readily visible in the original temporarily dependent ultrasound image.

In a further aspect of the present invention an interventional apparatus for performing an interventional procedure with respect to an object is presented, wherein the interventional apparatus comprises:

an interventional element for performing the interventional procedure with respect to the object, an ultrasound data visualization apparatus for visualizing ultrasound data of the object as defined in claim 1.

In another apsect of the present invention an ultrasound data visualization method for visualizing ultrasound data showing an object during an interventional procedure is presented, wherein the ultrasound data visualization method comprises:

providing a temporally dependent ultrasound image of the object by an ultrasound image providing unit, determining a current image of the object based on a part of the temporally dependent ultrasound image, which corresponds to a current time interval, by a current image determining unit, determining a reference image of the object based on a part of the temporally dependent ultrasound image, which corresponds to a reference time interval, wherein the reference time interval and the current time interval correspond to different phases of the interventional procedure, by a reference image determining unit, simultaneously displaying the reference image and the current image by a display.

In another aspect of the present invention a ultrasound data visualization computer program for visualizing ultrasound data showing an object during an interventional procedure is presented, wherein the computer program comprises program code means for causing an ultrasound data visualization apparatus defined in claim 1 to carry out the steps of the ultrasound data visualization method as defined in claim 14, when the computer program is run on a computer controlling the ultrasound data visualization apparatus.

It shall be understood that the ultrasound data visualization apparatus of claim 1, the energy application apparatus of claim 13, the ultrasound data visualization method of claim 14 and the ultrasound data visualization computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
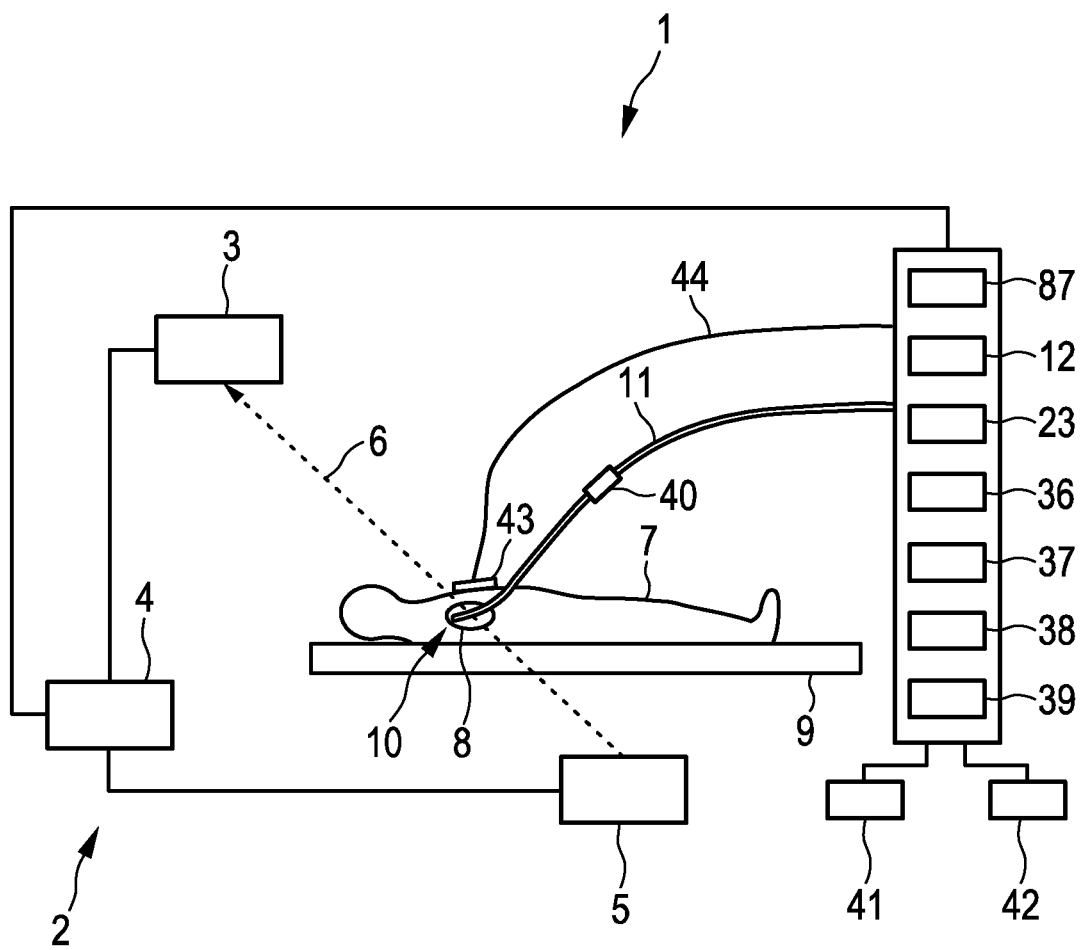
FIG. 1 shows schematically and exemplarily an embodiment of an energy application apparatus for applying energy to an object.

FIG. 1 shows schematically and exemplarily an embodiment of an interventional apparatus for performing an interventional procedure with respect to an object. In this embodiment the interventional apparatus is an energy application apparatus for applying energy to the object, particularly an ablation apparatus for ablating cardiac tissue. The ablation apparatus 1 comprises an energy application element 11 being an ablation catheter. The ablation catheter 11 is introduced into the heart 8 of a person 7 lying on a support unit 9 like a patient table. The tip 10 of the ablation catheter 11 is schematically and exemplarily shown in more detail in FIG. 2.

Figure 2:
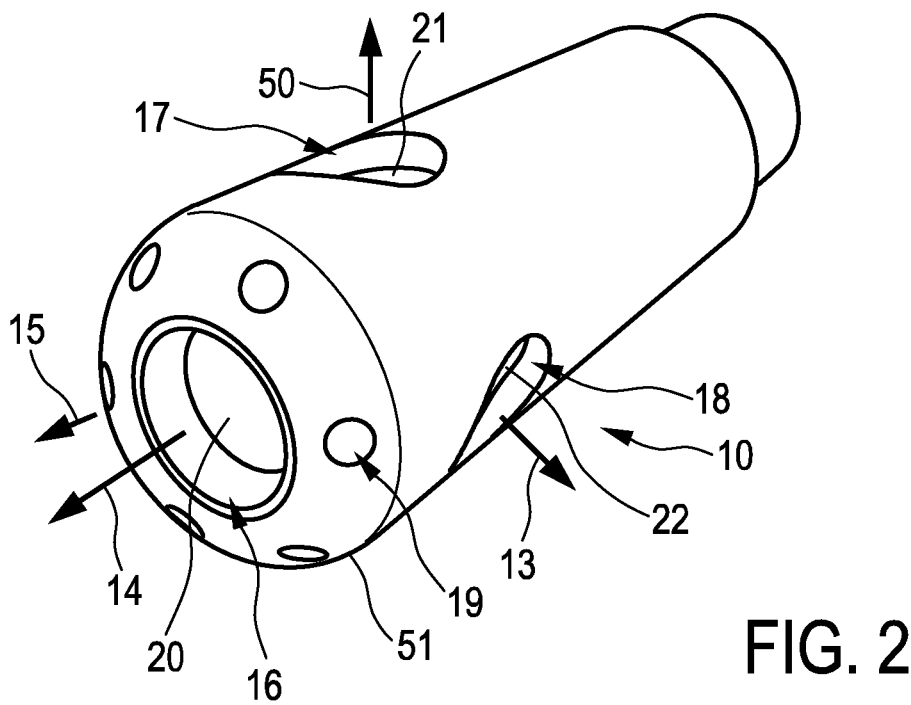
FIG. 2 shows schematically and exemplarily and embodiment of a tip of an ablation catheter of the energy application apparatus shown in FIG. 1.

The tip 10 of the ablation catheter 11 comprises a frontal ultrasound transducer 20 for acquiring first ultrasound data in a first acquisition direction 14 being a frontal direction with respect to the tip 10 of the ablation catheter 11 and three lateral transducers, of which only two transducers 21, 22 are visible in FIG. 2, for acquiring second, third and fourth ultrasound data in second, third and fourth acquisition directions 50, 13, 15 being lateral directions.

The frontal transducer 20 can be regarded as being an axial transducer acquiring the first ultrasound data in the axial direction 14 being the first acquisition direction. Moreover, in this embodiment the tip 10 of the ablation catheter 11 is substantially circular in cross section such that the lateral directions 50, 13, 15 can be regarded as being radial directions and the respective lateral transducers can be regarded as being radial transducers.

The tip 10 of the ablation catheter 11 further comprises an ablation electrode 51 comprising an axial opening 16 and lateral openings 17, 18, through which the ultrasound transducers can acquire the ultrasound data. Moreover, the ablation electrode 51 comprises irrigation openings 19 for allowing irrigation fluid flowing within the ablation catheter 11 to leave the tip 10 of the ablation catheter 11.

The ablation electrode 51 is electrically connected with an ablation control unit 37 by using an electrical conductor like a wire (not shown in FIG. 2 for clarity reasons), in order to allow a physician to control the application of ablation energy. In this embodiment the ablation control unit 37 comprises a radio frequency source for applying radio frequency energy to the cardiac tissue for ablating the same. The ablation apparatus 1 further comprises an irrigation control unit 38 for controlling the flow of the irrigation fluid within the ablation catheter 11 and, thus, for controlling the irrigation fluid leaving the tip 10 of the ablation catheter 11 through the irrigation openings 19. The ablation catheter 11 comprises a lumen for guiding the fluid from the irrigation control unit 38 to the irrigation openings 19. The irrigation control unit 38 preferentially comprises a fluid source and a pump for providing fluid to the tip 10 of the ablation catheter 11.

The ablation apparatus 1 further comprises an ultrasound control unit 12, which is electrically connected to the ultrasound transducers in the tip 10 of the ablation catheter 11 via electrical connections like electrical wires (not shown in FIG. 2 for clarity reasons). The ultrasound control unit 12 and the ultrasound transducers in the tip 10 of the ablation catheter 11 are preferentially configured such that M-mode images are acquired in the different acquisition directions as temporally dependent ultrasound images.

The ablation apparatus 1 is used for performing and for monitoring the cardiac ablation procedure. The ablation apparatus 1 is particularly adapted to cure cardiac arrhythmia. The ultrasound transducers in the tip 10 of the ablation catheter 11 enable a physician in an electrophysiology laboratory to assess in realtime certain relevant parameters of the heart wall from the inside. This will in the following exemplarily be illustrated with reference to FIG. 3.

Figure 3:
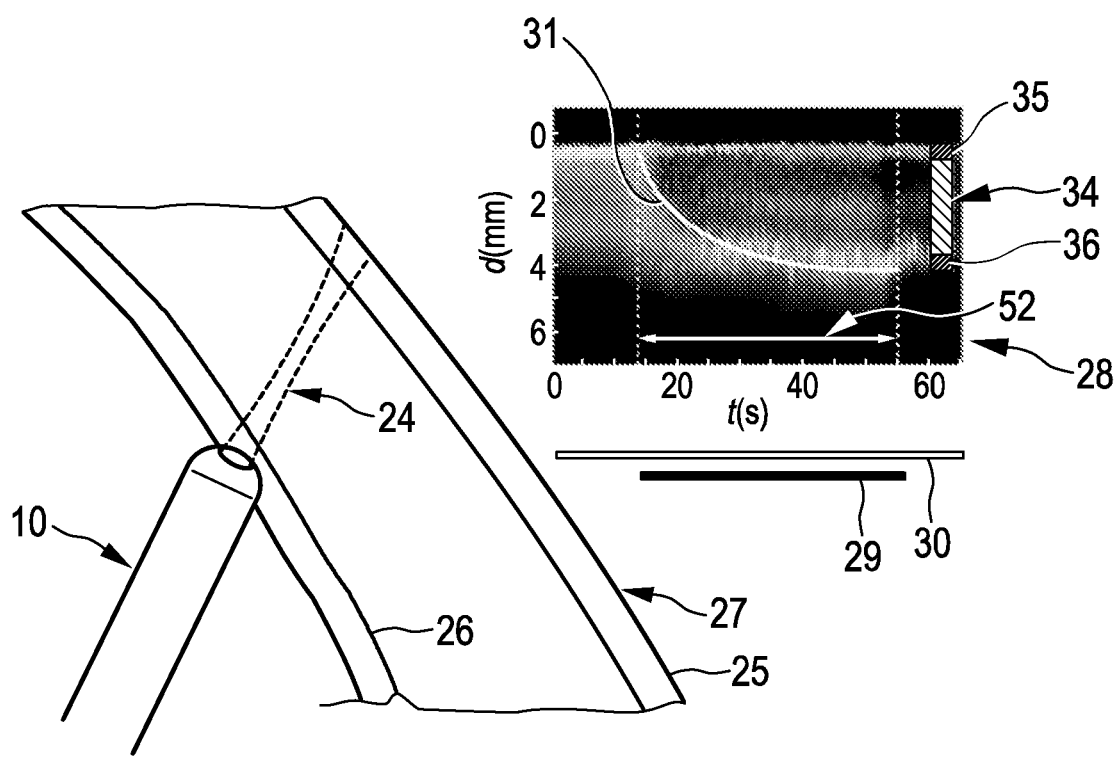
FIG. 3 shows schematically and exemplarily the tip of the ablation catheter at a location on a heart wall.

FIG. 3 shows the tip 10 of the ablation catheter 11 acquiring ultrasound data by using the axial frontal transducer in the first acquisition direction. A corresponding ultrasound beam is schematically indicated in FIG. 3 by broken lines 24. The ultrasound waves are sent into a heart wall 27 and scattered and/or reflected ultrasound waves are received by the frontal axial transducer at the tip 10 of the ablation catheter 11. Resulting temporally dependent ultrasound data, i.e. in this embodiment a resulting M-mode image 28, is exemplarily shown in the upper right part of FIG. 3. The M-mode image 28 shows the ultrasound signal amplitude depending on the depth d in millimeters and depending on the time t in s. The line 30 indicates the duration of ultrasound monitoring and the lines 29, 52 indicate the duration of applying ablation energy to the cardiac tissue. The line 31 indicates the ablation depth and the column 34 indicates the position of a front side 26 of the heart wall 27 by using the block 35 and the ablation depth by using the block 36. By visual inspection of the ultrasound M-mode image 28 the physician can measure the heart wall thickness, i.e. the positions of the front side 26 and the back side 25 of the heart wall 27, and can then decide on the best ablation regime like the optimal ablation power, the optimal flow rate of the irrigation fluid being preferentially a saline cooling fluid and the optimal ablation duration. During the application of the ablation energy the lesion formation can be monitored, wherein the physician can halt the ablation procedure, when a lesion has become transmural, i.e. when the treatment reached the back side 25 of the heart wall 27. In case steam pockets are formed inside the cardiac tissue, the physician can see this formation in the M-mode image 28 and can halt the ablation procedure to prevent a tissue rupture, i.e. to prevent a so-called "pop".

Figure 4:
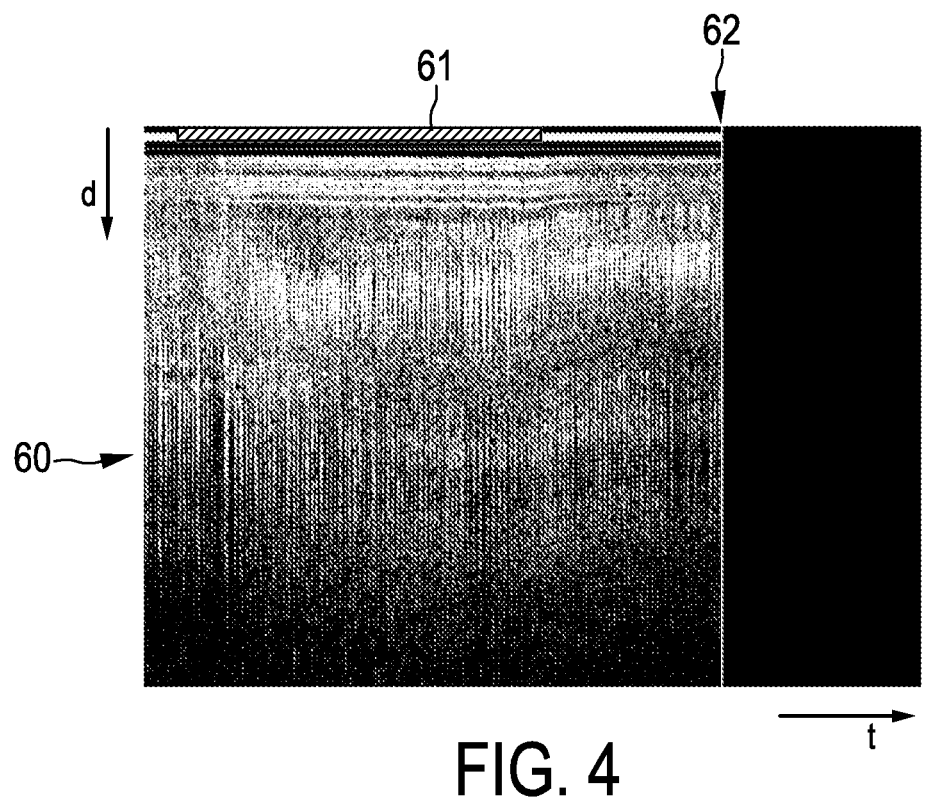
FIG. 4 shows exemplarily a conventional M-mode image over a relatively large time span.

FIG. 4 shows schematically and exemplarily an M-mode image 60, which may be obtained during a cardiac ablation procedure. In FIG. 4 each vertical line is an A-line obtained after envelope detection of raw ultrasound RF-lines and further processing such as noise suppression and contrast enhancement. In FIG. 4 the vertical axis represents the depth d and the horizontal axis represents the time t. As time progresses, new A-lines are appended on the right side of the time cursor 62 in the M-mode image 60. If the region on the right-hand side of the white line 62 shown in FIG. 4 is also filled with A-lines, the white line 62, i.e. the time cursor, wraps to the left and overwrites the previously acquired A-lines. In FIG. 4 the ablation period, i.e. the period during which ablation power is applied, is indicated by the bar 61. The complete M-mode image may cover a time period of about 1 to 2 minutes. FIG. 4 shows temporarily dependent ultrasound data in a pre-object-influence phase, in an object-influence phase and in an opposed-object-influence phase. In the object-influence phase the object, i.e. in this embodiment the cardiac tissue, is influenced at a location on the object by applying energy to the object. The respective time period is indicated by the line 61.

Figure 5:
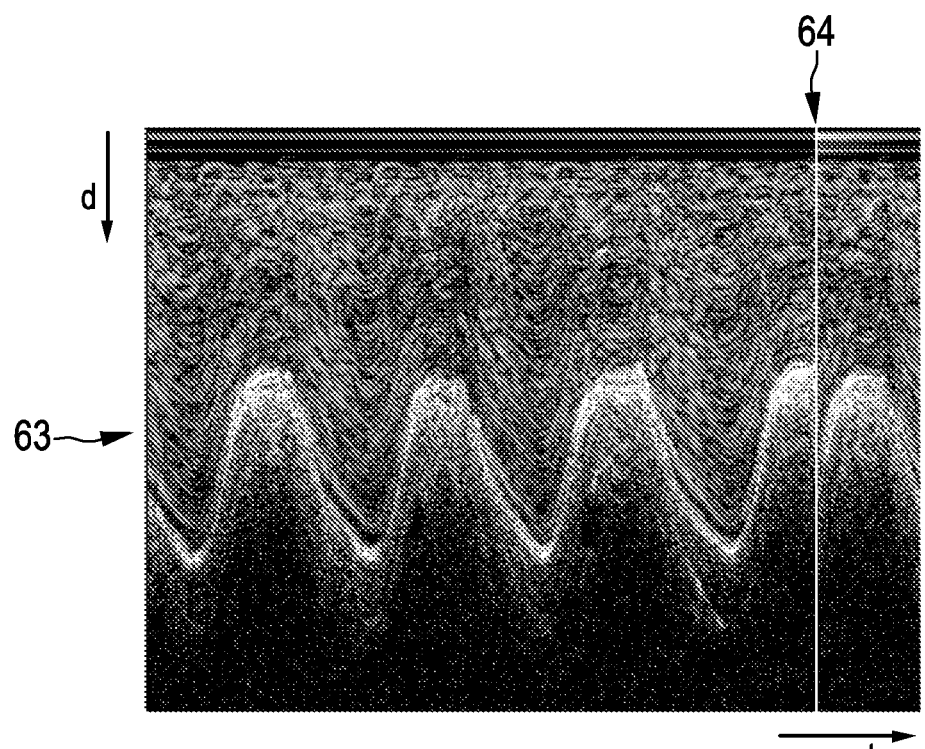
FIG. 5 shows exemplarily a conventional M-mode image over a relatively short time span.

FIG. 5 shows exemplarily a further M-mode image 63 with a time cursor 64, wherein in this example the M-mode image 63 covers a time span of 4 seconds, i.e. the M-mode image 63 exemplarily shown in FIG. 5 is shown with a much larger temporal resolution than the M-mode image 60 exemplarily shown in FIG. 4. If the relatively short time span is chosen as exemplarily shown in FIG. 5, much more details are visible in the M-mode image. This high level of detail can reveal important information like the variation of the cardiac backwall, which is related to the local heart wall thickness. However, when inspecting high detail information on the short time span, the physician looses the ability to observe tissue changes occurring at a much larger time scale as shown in the M-mode image 60 of FIG. 4. In contrast, the M-mode image 60 shown in FIG. 4 provides the ability to compare data acquired in realtime during ablation with data prior to ablation such that tissue changes that are indicative of lesion formation can be observed. Moreover, the large time span M-mode image 60 shown in FIG. 4 provides the ability to compare data acquired in realtime after ablation with data acquired prior to ablation and with data in the final phase of ablation such that the settling of the cardiac tissue during cooling down can be observed. These comparisons can not be performed by using the short time span M-mode image 63 exemplarily shown in FIG. 5.

The ablation apparatus is therefore adapted to provide an ultrasound data visualization, which allows for an observation of high detail M-mode images, while tissue changes occurring due to ablation can still be observed over several phases of the interventional procedure.

The ultrasound transducers 20, 21, 22 and the ultrasound control unit 12 can be regarded as being an ultrasound image providing unit for providing a temporally dependent ultrasound image of the cardiac tissue, wherein the temporally dependent ultrasound image is an M-mode image. The ablation apparatus comprises a current image determining unit for determining a current image of the object based on a part of the temporally dependent ultrasound image, which corresponds to a current time interval, and a reference image determining unit 36 for determining a reference image of the object based on a part of the temporally dependent ultrasound image, which corresponds to a reference time interval, wherein the reference time interval and the current time interval correspond to different phases of the interventional procedure being, in this embodiment, an ablation procedure for ablating the cardiac tissue at a location by applying energy to the cardiac tissue. The ablation apparatus 1 further comprises a display 42 for simultaneously displaying the reference image and the current image.

The ultrasound image providing unit 12, 20, 21, 22 and the current image determining unit 23 are preferentially adapted to continuously update the current image in a wrapping fashion as it is known for the updating of M-mode images, whereas the reference image preferentially stays constant at least over a certain time.

The reference image and the current image correspond to different phases of the ablation procedure, wherein the phases are a pre-object-influence phase, an object-influence-phase and a post-object-influence-phase. For instance, the reference time interval can correspond to a pre-object-influence phase being a pre-ablation phase and the current time interval can correspond to an object-influence phase during which ablation energy is applied to the object. Or, the reference time interval can correspond to the object-influence phase and the current time interval can correspond to the post-object-influence phase being, in this example, a post-ablation phase, in which the ablation procedure has been completed.

The ablation apparatus 1 can be adapted to show in the pre-object-influence phase, i.e. prior to ablation, a conventional M-mode image with a relatively short time span of, for instance, two seconds, wherein the A-lines are appended in the above-mentioned wrap around manner as exemplarily shown in FIG. 5. When ablation has been started, the last segment of the M-mode image prior to ablation is preferentially selected for the reference image. Therefore, the ablation apparatus comprises preferentially an energy application time providing unit for providing a start time, at which the object-influence phase starts, wherein the reference image determining unit 36 can be adapted to determine the reference time interval depending on the provided start time and to determine the reference image based on the part of the temporally dependent ultrasound image, i.e. the part of the M-mode image, which corresponds to the determined reference time interval. In particular, the reference image determining unit 36 can be adapted to determine the reference time interval as a time interval immediately before the provided start time. This is illustrated in FIG. 6.

Figure 6:
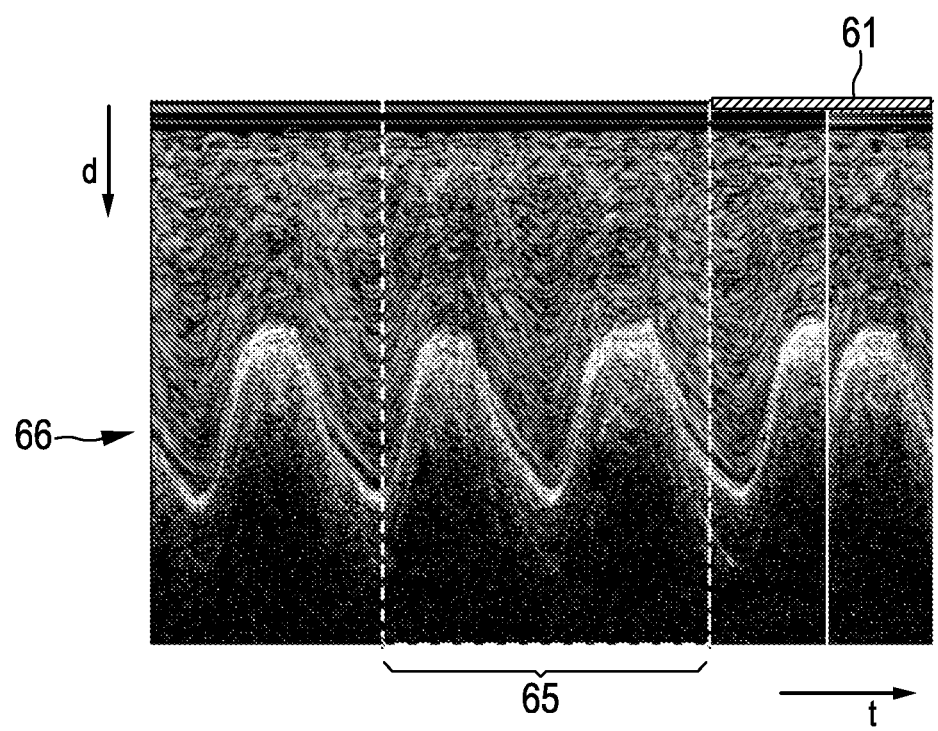
FIG. 6 illustrates the determination of a reference image from an M-mode image.

FIG. 6 shows an M-mode image 66 with a relatively short time span of, for instance, two to three seconds in the pre-object-influence phase, which is present before the object-influence phase indicated by the line 61, and in the object-influence phase. A last segment 65 of the M-mode image 66, which is located immediately before the start time of starting the ablation procedure and which covers a time span of about two seconds, is selected as reference image. The short time span of about two seconds is preferred in the present case, because it corresponds to a single heartbeat cycle at a lowest assumed heart rate of 30 beats per minute. It should be noted that FIG. 6 may not be shown on the display 42. FIG. 6 is only shown here to illustrate the determination of the reference image.

In this embodiment, the energy application time providing unit is the ablation control unit 37, wherein the ablation control unit 37 is adapted to send a signal to the reference image determining unit 36 for prompting the reference image determining unit 36 to determine the reference image, if the ablation control unit 37 controls the ablation catheter such that energy is applied to the cardiac tissue.

Figure 7:
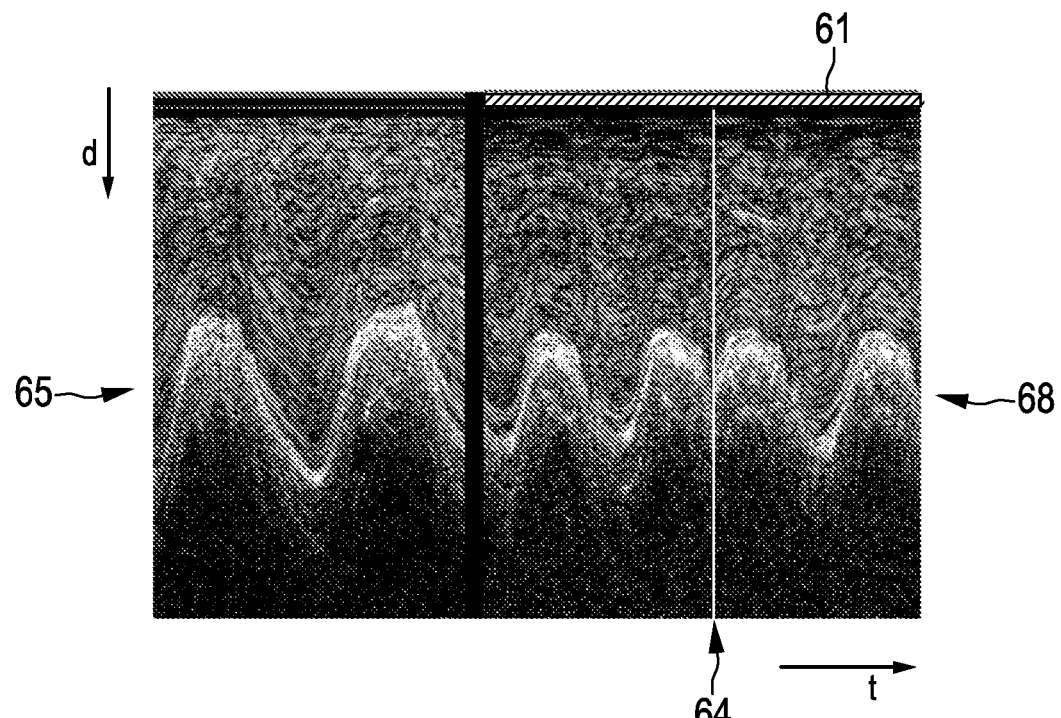
FIG. 7 shows exemplarily a reference image corresponding to a pre-object-influence phase and a current image corresponding to an object-influence phase.

On the display 42 the reference image 65 is shown separately from the current image 68 as illustrated in FIG. 7. The current image continues to be updated in a wrapping fashion as it is known from conventional M-mode images. The corresponding time cursor line is referenced in FIG. 7 by the reference number 64. The reference image 65 stays constant. The reference image 65 and, thus, the reference time interval correspond to the pre-object-influence phase and the current image 68 and, thus, the current time interval correspond to the object-influence phase. In FIG. 7 the line 61 indicates the time duration, during which energy is applied to the cardiac tissue. As can be seen in FIG. 7, the heartbeat rate has increased during the ablation relative to the heartbeat rate before ablation.

Figure 8:
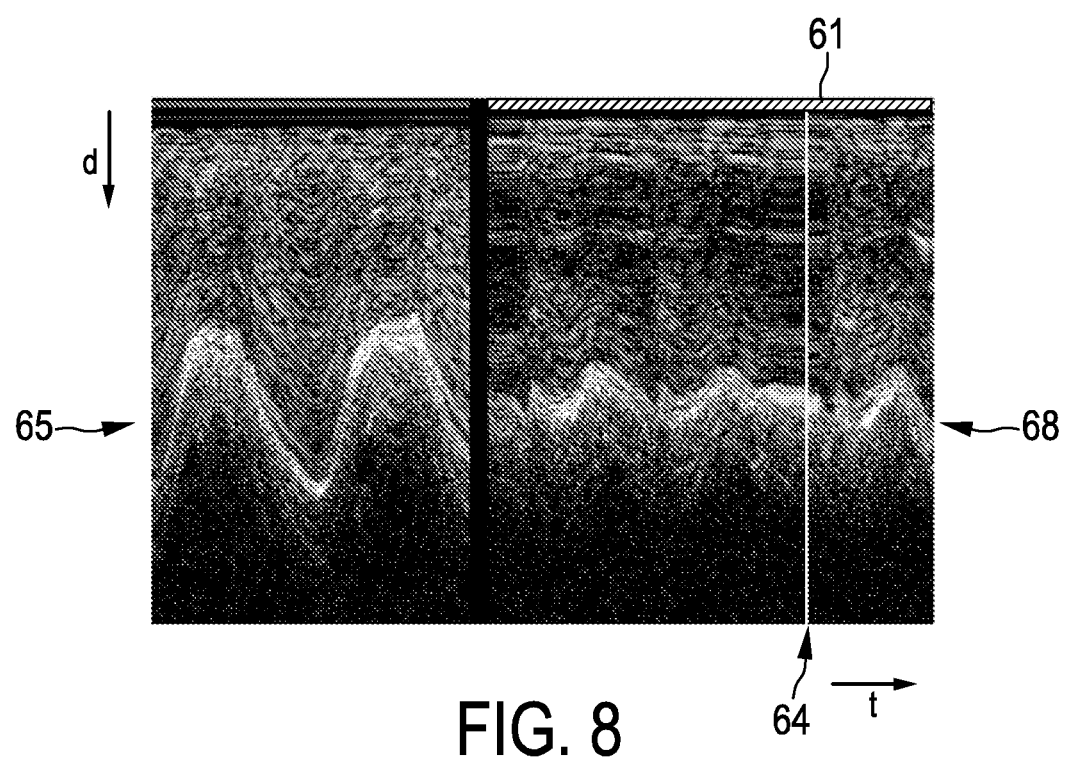
FIG. 8 shows exemplarily the reference image corresponding to the pre-object-influence phase and a current image corresponding to the object-influence phase at a later time in comparison to the time of the current image exemplarily shown in FIG. 7.

FIG. 8 shows exemplarily the reference image 65 and the current image 68, which are shown on the display unit 42, somewhat later in time, wherein the current image 68 and, thus, the current time interval still correspond to the object-influence phase. As can be seen in FIG. 8, the current tissue structure has changed compared to the structure shown in the reference image, i.e. the local tissue mobility has decreased due to necrosis.

Figure 9:
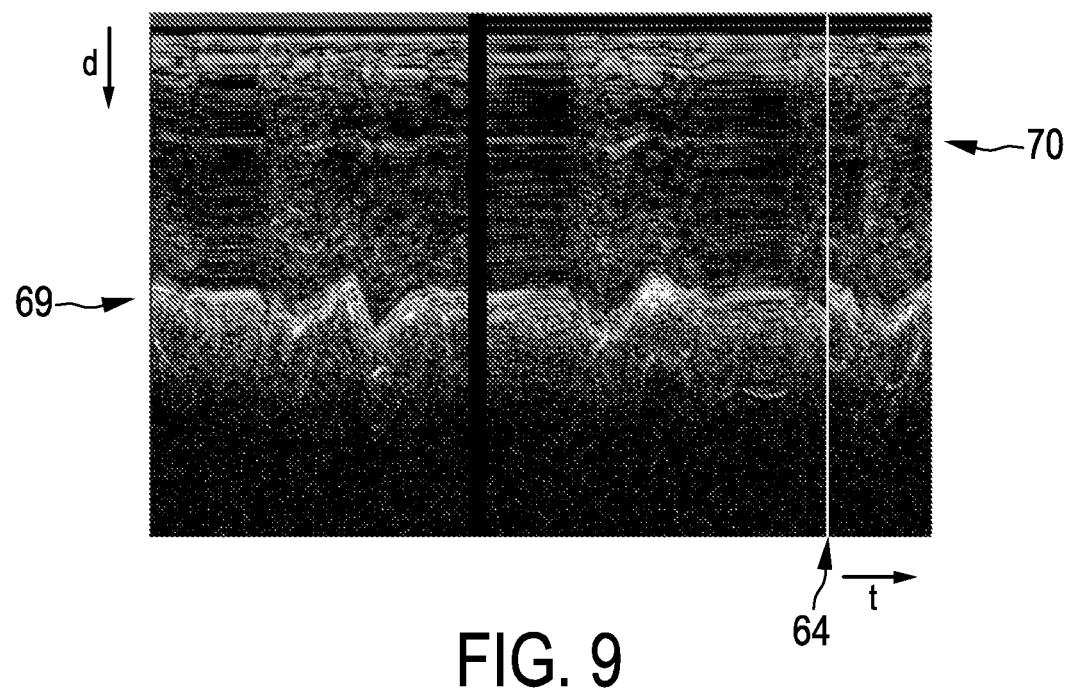
FIG. 9 shows exemplarily a reference image, which corresponds to a last part of the object-influence phase and a current image, which corresponds to a post-object-influence phase.

The reference image determining unit 38 is adapted to update the reference image to contain a last time segment of, for instance, two seconds of the object-influence phase being in this example an ablation period, when the application of the energy is stopped. The energy application time providing unit is therefore preferentially also adapted to provide an end time at which the object-influence phase ends, wherein the reference image determining unit 36 is adapted to determine the reference time interval depending on the provided end time and to determine the reference image based on the part of the temporally dependent ultrasound image, i.e. the M-mode image, which corresponds to the determined reference time interval. In particular, the reference image determining unit is preferentially adapted to determine the reference time interval as a time interval, which has a fixed temporal duration and which is arranged immediately before the provided end time. In this embodiment, the energy application time providing unit is the ablation control unit 37 providing a signal to the reference image determining unit 36 indicating, when the application of the ablation energy has been stopped. FIG. 9 exemplarily shows such a reference image 69, which corresponds to the time interval immediately before the object-influence phase stops, and the current image 70, which may be shown on the display 42. In this example, the reference image belongs to the object-influence phase and the current image belongs to the post-object-influence phase. In another embodiment, the reference image may not be updated such that, after the application of the ablation energy has stopped, the reference image still shows pre-ablation data for comparing these data with live data shown by the current image.

The time span for the reference data, i.e. the reference time interval defining the reference image, can be automatically determined based on the onset of the application of the ablation energy. This onset, i.e. the start of the object-influence phase, can be indicated by a signal received from the ablation control unit 37 as described above with reference to FIG. 7. However, the energy application time providing unit can also be a separate unit detecting the onset of the application of the ablation energy from the M-mode image. Moreover, an input device 41 of the ablation apparatus 1 can be used for allowing a user to input the time of the onset of the application of the ablation energy. Thus, also the input device 41 can be regarded as being an energy application time providing unit. After the onset of ablation, i.e. the start time at which the object-influence phase starts, has been indicated, the reference time interval can be defined as the time interval of, for instance, two seconds in the past starting from the onset time. The reference time interval and, thus, the reference image, can also be selected completely manually by using the input device 41. Also the end time at which the object-influence phase ends and a corresponding determination of a reference image can be based on an end time, which a) can be provided manually by using the input device 41, b) can be provided by the ablation control unit 37 or c) can be determined from the M-mode image.

FIGS. 4 to 9 show ultrasound data acquired by a single ultrasound transducer only. However, the ablation apparatus 1 can also be adapted to show ultrasound data on the display 42 acquired by more than one of the ultrasound transducers. For instance, as exemplarily shown in FIG. 10, the display 42 can show four reference images 73 . . . 76, which correspond to the four ultrasound transducers at the tip 10 of the ablation catheter 11, in a reference region 71 of the display 42. Correspondingly, the display unit 42 can show four current images 80 ... 83, which correspond to the four ultrasound transducers, in a live data region 72 of the display 42.

The ablation apparatus 1 further comprises a physiological signal providing unit for providing a temporally dependent physiological signal corresponding to the reference and current time intervals, wherein the display 42 is adapted to simultaneously display the provided physiological signal and the current and reference images and wherein the provided physiological signal and the current and reference images are temporally aligned on the display 42. In this embodiment, the physiological signal providing unit comprises electrocardiography electrodes 43 arranged on the breast of the person 7, wherein the electrocardiography electrodes 43 are electrically connected with an electrocardiography control unit 87 via electrical connections 44 like electrical wires. Reference electrocardiogram (ECG) data 77 and current ECG data 84 are shown on the display 42 temporally aligned with the reference and current ultrasound images 73 ... 76, 80 ... 83. Thus, especially for the fast refresh rate, i.e. especially for the relatively short time spans of the reference and current ultrasound images, the visualization of the ultrasound data can be linked with the visualization of electrogram recordings such that the timing of reference and live data from both sources are aligned.

The display 42 can be adapted to show further reference ECG or electrogram (EGM) data 78, 79 and corresponding further current ECG or EGM data 85, 86 temporally aligned with the reference and current ultrasound images 73 ... 76, 80 ... 83. The ECG data may be measured by further electrocardiography electrodes and the EGM data may be measured by corresponding electrodes on the tip of the ablation catheter not shown in FIG. 2.

Figure 10:
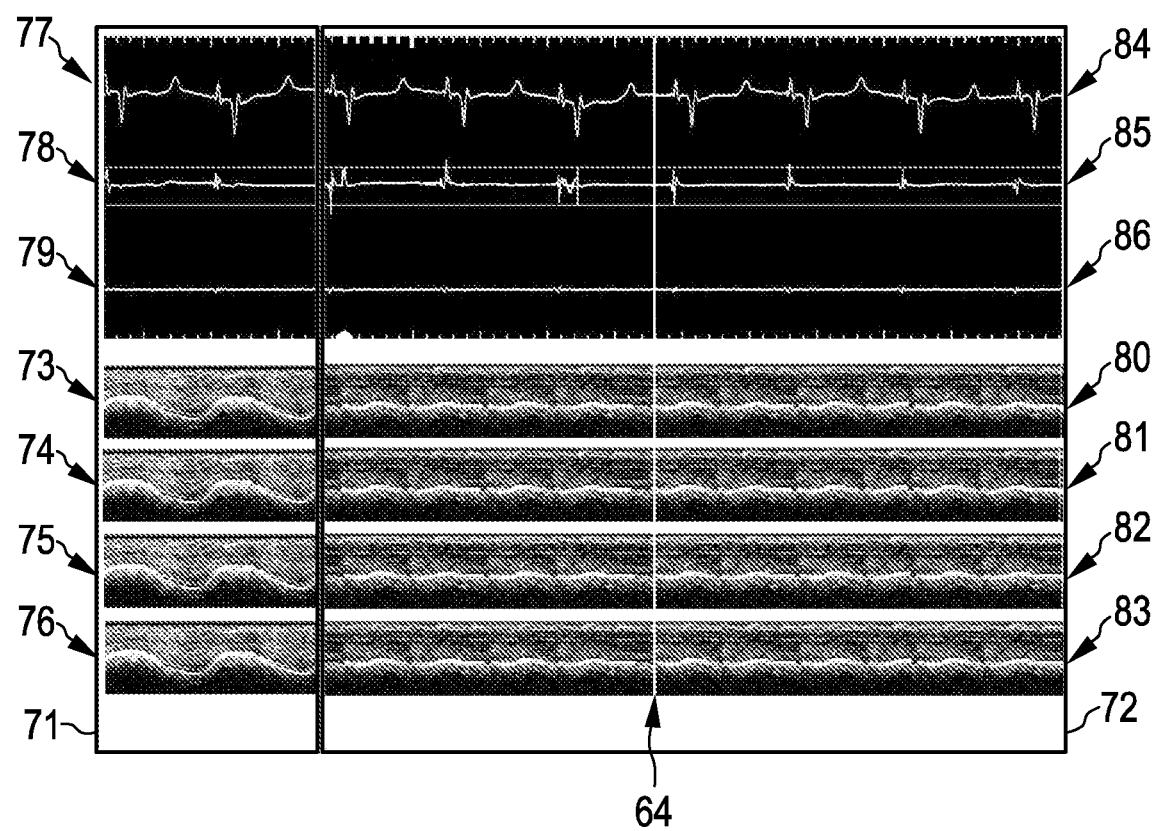
FIG. 10 shows exemplarily reference and current images, which have been acquired by different ultrasound transducers and which are temporally aligned with an electrocardiography signal.

Although in FIG. 10 ultrasound data of all four ultrasound transducers are shown, it is of course also possible that the display 42 shows ultrasound data of one, two or three ultrasound transducers only. It may be selectable by the user via the input device 41, which ultrasound data of the ultrasound transducers are shown on the display 42. However, the display 42 or another unit of the ablation apparatus can also be adapted to automatically select one or several ultrasound transducers, of which the ultrasound data are displayed.

In FIGS. 7 to 10, the current time interval and the reference time interval are relatively small. For instance, they may cover about some seconds. But, the temporal distance between the current time interval and the reference time interval can be relatively large. For example, if the reference image shows cardiac tissue before the ablation procedure has been started and if the current image shows the cardiac tissue at the end of the ablation procedure, the temporal distance between the reference time interval and the current time interval can be about one or two minutes.

Figure 11:
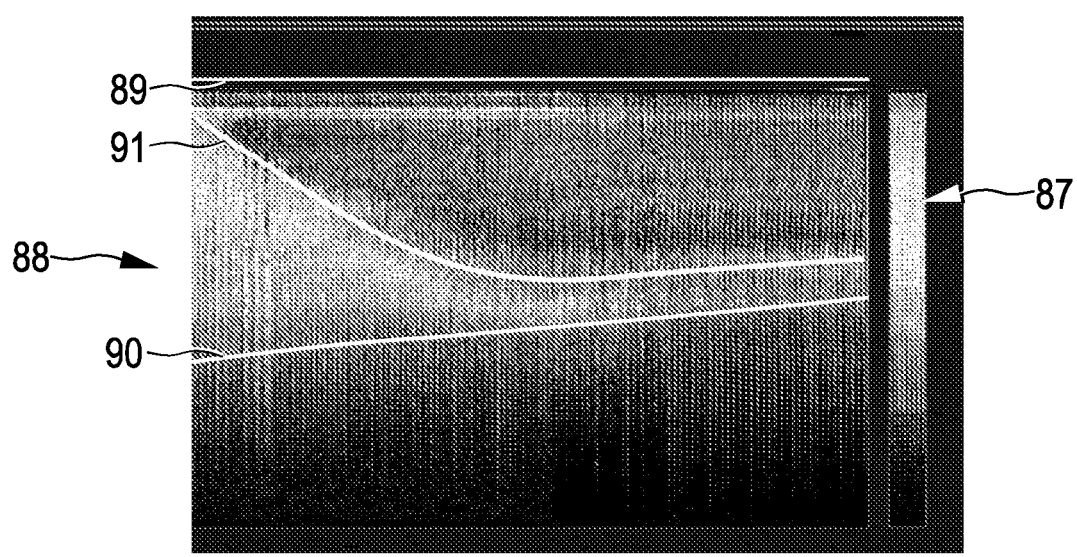
FIG. 11 shows exemplarily a reference image and a current image over a relatively large time span.

Although in above described embodiments the time span of the ultrasound images is relatively short, for instance, only a few seconds, the time span of the ultrasound images shown on the display 42 can also be longer, for instance, one or two minutes. FIG. 11 shows exemplarily such a situation, in which the time spans are longer.

In FIG. 11, a reference ultrasound image 87 is shown, which corresponds to a pre-object-influence phase before ablation energy has been applied to the cardiac tissue. Moreover, a current image 88 is shown, which represents the object-influence phase. In FIG. 11, the lines 89, 91 indicate the lesion formation due to the application of the energy and the line 90 indicates the location of the back side of the heart wall to which the ablation energy is applied. The current image determining unit 23 or another unit of the ablation apparatus 1 can be adapted to automatically detect the lesion formation and the position of the back side from the ultrasound data for allowing the display 42 to show the lines 89, 90, 91. Thus, also if the refresh rate of the ultrasound images is slower, reference data can be shown next to live data, in order to facilitate the interpretation of the ultrasound data.

In the above described embodiments the current image determining unit 23 is adapted to determine the current image as a part of the provided temporally dependent ultrasound image, i.e. as a part of the M-mode image, which corresponds to the current time interval, and the reference image determining unit is adapted to determine the reference image as a part of the provided temporally dependent ultrasound image, which corresponds to the reference time interval. However, the current image determining unit can also be adapted to determine the current image as a part of a processed image obtained by processing the provided temporally dependent ultrasound image, which corresponds to the current time interval, and the reference image determining unit can be adapted to determine the reference image as a part of the process image, which corresponds to the reference time interval. The processed image is, for instance, a motion image, a strain image, a gated image or a likelihood image indicating the likelihood that a certain image element represents a certain part of the object.

For instance, the electrocardiography electrodes together with the electrocardiography control unit can provide an electrocardiography signal as a repetitive signal being indicative of the motion of the heart to be ablated. The combination of the electrocardiography electrodes and the electrocardiography control unit can therefore be regarded as being a repetitive signal providing unit. In other embodiments the repetitive signal can also be provided in another way, for instance, it may be determined from the M-mode image. The repetitive signal providing unit can therefore also be a calculation unit for determining the repetitive signal from the M-mode image. The current image determining unit and the reference image determining unit can be adapted to determine gated reference and current images for the reference and current time intervals, respectively, based on the provided repetitive signal and the provided temporally dependent ultrasound image, i.e. the provided M-mode image. For example, based on the electrocardiography signal it can be determined which A-line corresponds to which cardiac phase, wherein for determining a gated M-mode image for a certain cardiac phase the A-lines corresponding to this certain cardiac phase can be combined. A gated M-mode image, which has been determined for a cardiac phase in such a way, can be regarded as being a static gated M-mode image in comparison to a dynamic gated M-mode image, which is preferentially formed by showing gated M-mode images, which correspond to different cardiac phases, temporally consecutively at the same location on the display for showing how the M-mode image changes over a cardiac cycle. The A-lines forming a gated static or dynamic reference image correspond preferentially to the pre-object-influence phase or the object-influence phase and the A-lines forming a gated static or dynamic current image correspond to another phase, i.e. the object-influence phase or the post-object-influence phase.

For processing the ultrasound image such that it is transformed to a strain image well-known strain transformation algorithms can be used for generating an image, where at each location in the image a grey level value is shown that corresponds to a local strain value. For generating a motion image known motion detection algorithms can be used, wherein the resulting motion image can be color-coded such that each location in the image represents a local tissue motion magnitude and potentially also a motion direction. The likelihood image can be an image, where at each location in the image a grey value is shown, which indicates a degree of correspondence with a certain tissue type.

The tip 10 of the ablation catheter 11 can be moved to a first location on the heart wall, wherein, after the first location has been reached, ablation energy can be applied to the cardiac tissue for ablating the cardiac tissue at this location. During the application of the ablation energy, the physician can see the current image and the reference image on the display 42, wherein based on his/her observations the physician can halt the application of the ablation energy at a suitable time. After the application of the ablation energy has been completed at the first location, the tip 10 of the ablation catheter 11 can be moved to a second location on the heart wall for performing this ablation procedure also at this second location. The tip 10 of the ablation catheter 11 can then be moved to further locations for ablating the cardiac tissue also at these locations.

The reference image determining unit 36 knows when energy is applied and when it is not applied and can therefore distinguish between the pre-object-influence phase, the object-influence phase and the post-object-influence phase. The reference image determining unit 36 can therefore determine the reference image such that it corresponds to a desired phase, in particular, to the pre-object-influence phase or the object-influence phase. However, the ablation apparatus 1 can be also configured to allow the reference image determining unit to distinguish between different phases, if during the movement of the tip 10 of the ablation catheter 11 from one location to another, the application of the ablation energy is not switched off. In particular, the ablation apparatus 1 can comprise a location change signal providing unit 40 being, in this embodiment, a hand grip comprising a push button for providing a location change signal indicating when the tip 10 of the ablation catheter 11 has reached a new location at which the cardiac tissue is to be ablated, wherein the reference image determining unit can be adapted to determine the time interval immediately after the tip 10 of the ablation catheter 11 has reached the new location as the reference time interval depending on the provided location change signal and to determine the reference image based on the part of the temporally dependent ultrasound image, which corresponds to the determined reference time interval. Thus, the ablation apparatus can also be adapted to be used in an ablation procedure called "drag-and-ablate", in which the physician moves at distinct moments the tip of the ablation catheter, while ablation power remains to be turned on, thereby creating overlapping lesions or a so-called "lesion line". In this scenario, where at different times during the ablation the catheter tip is at different heart wall locations, the pre-object-influence reference image that belongs to a first heart wall location looses much of its meaning. Therefore, for the drag-and-ablate scenario at the moment when during ablation power delivery the tip of the ablation catheter has just been moved to a next location, the reference image is updated with the newest group of A-lines, wherein it is assumed that, immediately after the tip of the ablation catheter has been moved to the next position, the cardiac tissue has not already been substantially influenced such that this newest group of A-lines immediately, after the catheter tip has reached the next location, can be regarded as defining a reference image of the last part of the pre-object-influence phase.

In order to determine such a reference image, the reference image determining unit needs to know when the tip of the ablation catheter is moved and when it halts at a new location. In the embodiment shown in FIG. 1 the location change signal providing unit 40 is formed by a hand grip with a push button, which provides a location change signal indicating when the tip of the ablation catheter has reached a new location. However, alternatively or in addition, a location change signal providing unit can be used, which determines when the tip of the ablation catheter halts at a new position, after it has been moved, in another way. For instance, the location change signal providing unit can be a calculation unit being adapted to determine this information automatically from the live ultrasound data, i.e. from the current image.

Referring again to FIG. 1, the ablation apparatus 1 further comprises a position detection system 2 for detecting the position of the tip 10 of the ablation catheter 11 within the person 7. In this embodiment the position detection system 2 is an x-ray fluoroscopy system, in particular, an x-ray C-arm system. The x-ray fluoroscopy system comprises an x-ray source 5 for generating x-rays 6 which traverse the person 7 on the table 9, wherein the x-rays 6, which have traversed the person 7, are detected by an x-ray detector 3. The x-ray fluoroscopy system 2 further comprises a fluoroscopy control unit 4 for controlling the x-ray source 5 and the x-ray detector 3. The x-ray detector 3 generates x-ray images of the person 7, which can be shown on the display 42. On the generated x-ray images the tip 10 of the ablation catheter 11 is visible within the person 7 such that the x-ray images show the position of the tip 10 of the ablation catheter 11 within the person 7. In other embodiments other position detection systems for detecting the position of the catheter tip within the person can be used like position detection systems which are based on electromagnetic sensors, ultrasound sensors, et cetera.

The ablation apparatus further comprises a navigation unit 39 for allowing the ablation catheter 11, in particular, the catheter tip 10, to be navigated to a desired location within the person 7. The navigation unit 39 can be adapted to allow a user to navigate the ablation catheter 11 completely by hand or semi-automatically. The ablation catheter 11 comprises built-in guiding means (not shown in FIG. 1), which can be controlled by the navigation unit 39. The ablation catheter 11 can, for example, be steered and navigated by the use of steering wires, in order to guide the catheter tip 10 to a desired location within the person 7.

Figure 12:
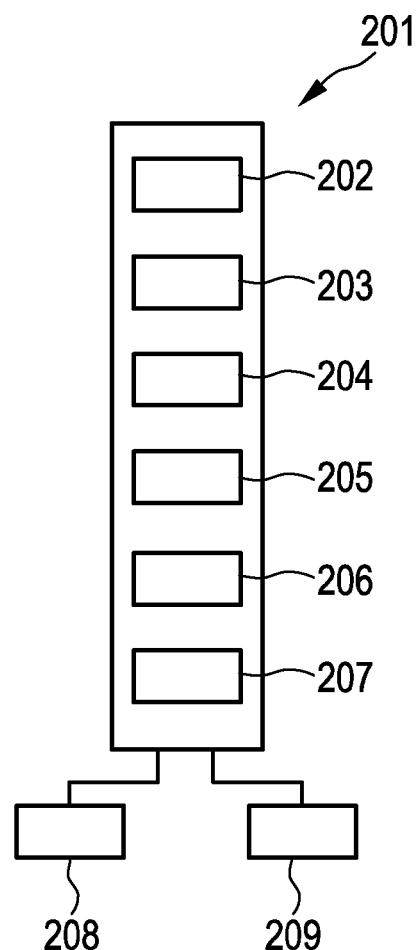
FIG. 12 shows schematically and exemplarily an embodiment of an ultrasound data visualization apparatus for visualizing ultrasound data of an object during an interventional procedure.

The ultrasound transducers, the ultrasound control unit, the current image determining unit, the reference image determining unit, the display, the energy application time providing unit, the location change signal providing unit, the input device and the physiological signal providing unit are used for determining and displaying the reference image and the current image and can therefore be regarded as forming an ultrasound data visualization apparatus being integrated with the ablation apparatus. However, the ultrasound data visualization apparatus can also be a separate apparatus as schematically and exemplarily shown in FIG. 12.

The ultrasound data visualization apparatus 201 comprises an ultrasound image providing unit 202 for providing a temporally dependent ultrasound image of the object being, in this embodiment, an M-mode image of cardiac tissue. The ultrasound image providing unit 202 can be, for instance, an M-mode image determining unit for determining an M-mode image based on received ultrasound signals or the ultrasound image providing unit 202 can just be a receiving unit for receiving the M-mode image and for providing the received M-mode image. The ultrasound data visualization apparatus 201 further comprises an energy application time providing unit 203 for providing a start time at which the object-influence phase starts and/or for providing an end time, at which the object-influence phase ends. Also the energy application time providing unit 203 can just be a receiving unit for receiving a signal indicating the start time and/or the end time from, for instance, an ablation control unit and for providing the corresponding start time and/or end time. However, the energy application time providing unit 203 can also be adapted to determine the start time and/or the end time from the temporally dependent ultrasound image, in particular, from the provided M-mode image. A location change signal providing unit 204 is adapted to provide a location change signal indicating when the tip of the ablation catheter has reached a new location at which the cardiac tissue is to be ablated. Also this unit can just be a receiving unit, wherein in this case the receiving unit is adapted to receive a location change signal from, for instance, a push button which can be pushed by a physician when a new location has been reached. The location change signal providing unit 204 can also be a calculation unit for determining the location change signal from the temporally dependent ultrasound image, in particular, from the provided M-mode image.

The ultrasound data visualization apparatus can further comprise a physiological signal providing unit 205 being adapted to receive a physiological signal like an electrocardiography signal from a corresponding measurement element and to provide the received physiological signal. The physiological signal providing unit 205 can further be adapted to process the physiological signal, for instance, to reduce noise in the physiological signal and to enhance the signal.

The ultrasound data visualization apparatus 201 further comprises a current image determining unit 206 and a reference image determining unit 207. The current image determining unit 206 is adapted to determine a current image of the object, in this embodiment, of the cardiac tissue, based on a part of the temporally dependent ultrasound image, which corresponds to a current time interval, and the reference image determining unit 207 is adapted to determine a reference image of the object based on a part of the temporally dependent ultrasound image, which corresponds to a reference time interval, wherein the reference time interval and the current time interval correspond to different phases of the ablation procedure.

The ultrasound data visualization apparatus further comprises an input unit 208 and a display 209. The input unit 208 can be adapted to, for instance, allow a user to input the reference time interval, whereas the display 209 is adapted to simultaneously display the reference image and the current image.

Figure 13:
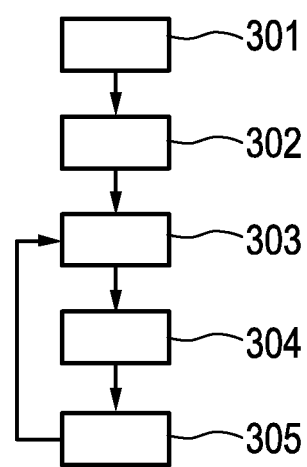
FIG. 13 shows a flowchart exemplarily illustrating an embodiment of an ultrasound data visualization method for visualizing ultrasound data showing an object during an interventional procedure.

In the following an embodiment of an ultrasound data visualization method for visualizing ultrasound data showing an object during an interventional procedure will exemplarily be described with reference to a flowchart shown in FIG. 13.

In this embodiment the interventional procedure is an ablation procedure and the object is cardiac tissue of a heart wall. In step 301 a temporally dependent ultrasound image of the cardiac tissue is provided by an ultrasound image providing unit. In this embodiment an M-mode image of the cardiac tissue is provided. In step 302 a reference image of the cardiac tissue is determined based on a part of the M-mode image, which corresponds to a reference time interval. For instance, in step 302 a reference time interval within a pre-object-influence phase and a corresponding reference image can be determined. In step 303 a current image of the cardiac tissue is determined based on a part of the M-mode image, which corresponds to a current time interval. The current time interval is in another phase of the ablation procedure than the reference time interval. For instance, the current time interval is within the object-influence phase. The length of the reference time interval and the current time interval can be defined by the temporal length of the respective regions on the display. In step 304 the reference image and the current image are simultaneously shown on the display. In step 305 the M-mode image, i.e. the corresponding A-lines, is further provided for updating the current image in step 303. Thus, steps 303, 304 and 305 are preferentially performed in a loop such that the current image is continuously updated in a wrapping fashion as known from conventional M-mode images.

Although in above described embodiments the interventional procedure is an ablation procedure, in other embodiments the ultrasound data visualization apparatus can also be adapted to visualize ultrasound data showing an object during another interventional procedure having different phases, wherein reference and current images corresponding to different phases can be displayed simultaneously.

Although in above described embodiments cardiac tissue has been influenced by applying energy to the cardiac tissue, wherein the application of energy to the cardiac tissue is monitored by using the ultrasound data visualization apparatus, in other embodiments the ultrasound data visualization apparatus can also be adapted to visualize ultrasound data of another object, for instance, of another part of a living being like another organ to which an interventional procedure is applied.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the current image, the determination of the reference image, the determination of a processed image, et cetera performed by one or several units or devices can be performed by any other number of units or devices. The procedures and/or the control of the ultrasound data visualization apparatus in accordance with the ultrasound data visualization method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an ultrasound data visualization apparatus for visualizing ultrasound data showing an object during an interventional procedure. A reference image and a current image of the object are simultaneously displayed, wherein the current image corresponds to a current time interval and the reference image corresponds to a reference time interval and wherein the current time interval and the reference time interval correspond to different phases of the interventional procedure. The current image can be shown therefore with, for instance, a relatively high temporal resolution for allowing a user to observe detailed object changes, which may be caused by the interventional procedure, while an overview over different phases of the interventional procedure can still be provided, because also the reference image is displayed and can be used by a user for comparing the current image with the reference image.

The invention claimed is:

1. An ultrasound data visualization apparatus for visualizing ultrasound data showing an object during an interventional procedure, the ultrasound data visualization apparatus comprising:
    an ultrasound image providing unit for providing a temporally dependent ultrasound image of the object;
    a reference image determining unit for automatically identifying a reference time interval and for extracting a reference image of the object, wherein the reference image of the object is a portion of the temporally dependent ultrasound image captured during the reference time interval;
    a current image determining unit for determining a current image of the object, based on a part of the temporally dependent ultrasound image, which corresponds to a current time interval, wherein the reference time interval and the current time interval correspond to different phases of the interventional procedure, and wherein the ultrasound image providing unit and the current image determining unit are configured to continuously update the current image by performing the following steps:
        adding newly acquired A-lines until the current image includes a maximum number of A-lines, and
        in response to the current image being updated to include the maximum number of A-lines, updating the current image replacing previously acquired A-lines of the current image, and not the reference image, with newly replacement acquired A-lines; and
    a display configured to simultaneously display the reference image and the continuously updated current image.

2. The ultrasound data visualization apparatus as defined in claim 1, wherein the ultrasound data visualization apparatus further comprises a physiological signal providing unit for providing a temporally dependent physiological signal corresponding to the reference and current time intervals, wherein the display is adapted to simultaneously display the provided physiological signal, the current image, and reference image in a temporally aligned manner on the display.

3. The ultrasound data visualization apparatus as defined in claim 1, wherein the ultrasound image providing unit and the current image determining unit are adapted to provide the current image in real time.

4. The ultrasound data visualization apparatus as defined in claim 1, wherein the ultrasound image providing unit is adapted to provide an M-mode image as the temporally dependent ultrasound image of the object.

5. The ultrasound data visualization apparatus as defined in claim 1, wherein the current time interval and the reference time interval are separated by a temporal distance and are smaller in duration than the temporal distance separating the current time interval and the reference time interval.

6. The ultrasound data visualization apparatus as defined in claim 1, wherein the current image determining unit is adapted to determine the current image as being said part of the provided temporally dependent ultrasound image or as being a processed image obtained by processing said part of the provided temporally dependent ultrasound image.

7. The ultrasound data visualization apparatus as defined in claim 1, wherein the temporally dependent ultrasound image is i) a motion image, ii) a strain image, iii) a gated image, if the object is a repetitively moving object, or iv) a likelihood image indicating the likelihood that a certain image element represents a certain part of the object.

8. An interventional apparatus for performing an interventional procedure with respect to an object, wherein the interventional apparatus comprises:
    an interventional element for performing the interventional procedure with respect to the object; and
    the ultrasound data visualization apparatus for visualizing ultrasound data of the object as defined in claim 1.

9. The ultrasound data visualization apparatus as defined in claim 1, wherein the ultrasound image providing unit and the current image determining unit continuously update the current image in a wrapping fashion.

10. The ultrasound data visualization apparatus as defined in claim 1, wherein the interventional procedure includes an object-influence phase during which the object is influenced at a location on the object by applying energy to the object by using an energy application element, a pre-object-influence phase and a post-object-influence phase, wherein the reference time interval and the current time interval correspond to different ones of these phases.

11. The ultrasound data visualization apparatus as defined in claim 10, wherein the ultrasound visualization apparatus comprises an energy application time providing unit for providing an end time at which the object-influence phase ends, wherein the reference image determining unit is adapted to identify the reference time interval depending on the provided end time.

12. The ultrasound data visualization apparatus as defined in claim 10, wherein during the interventional procedure, the energy application element is moved to different locations on the object for influencing the object at the different locations, wherein the ultrasound data visualization apparatus further comprises a location change signal providing unit for providing a location change signal indicating when the energy application element has reached a new location at which the object is to be influenced, wherein the reference image determining unit is adapted to identify a time interval immediately after the energy application element has reached the new location as the reference time interval in the pre-object-influence phase depending on the provided location change signal.

13. The ultrasound data visualization apparatus as defined in claim 10,
    wherein the ultrasound visualization apparatus comprises an energy application time providing unit for providing a start time at which the object-influence phase starts, and
    wherein the reference image determining unit is adapted to identify the reference time interval depending on the provided start time.

14. The ultrasound data visualization apparatus as defined in claim 10, wherein:
    the reference time interval includes the pre-object influence phase; and
    the current time interval includes at least one of the object influence phase and the post-object influence phase.

15. The ultrasound data visualization apparatus as defined in claim 10, wherein:

the reference time interval includes at least one of the pre-object influence phase and the object influence phase; and the current time interval includes the post-object influence phase.

16. The ultrasound data visualization apparatus as defined in claim 10, wherein:

the reference time interval includes the pre-object influence phase; and the current time interval includes the post-object influence phase.

17. An ultrasound data visualization method for visualizing ultrasound data showing an object during an interventional procedure that includes an object-influence phase during which the object is influenced at a location on the object by applying energy to the object by using an energy application element, a pre-object-influence phase preceding the object-influence phase in time and a post-object-influence phase after the object-influence phase in time, the ultrasound data visualization method comprising:

providing a temporally dependent ultrasound image of the object; and using a computer and a display to perform the following steps:

extracting a constant reference image of the object from the temporally dependent ultrasound image, wherein the constant reference image is automatically identified based on a part of the temporally dependent ultrasound image corresponding to a reference time interval, wherein the reference time interval corresponds to a prior phase of the interventional procedure, wherein the prior phase is different from and precedes a current phase of the interventional procedure in time, over a duration of the current phase of the interventional procedure, determining a continuously updating current image of the object based on a part of the temporally dependent ultrasound image, which corresponds to a current time interval, wherein the current time interval corresponds to the current phase of the interventional procedure and wherein the current time interval is less than the duration of the current phase, wherein said determining the continuously updating current image comprises:

adding newly acquired A-lines to the continuously updating current image until the continuously updating current image includes a maximum number of A-lines; and in response to the continuously updating image being updated to include the maximum number of A-lines, replacing previously acquired A-lines of the continuously updating current image, and not the constant reference image, with newly acquired replacement A-lines, over the duration of the current phase, simultaneously displaying, on the display, the constant reference image and the continuously updating current image.

18. A non-transitory computer-readable medium comprising computer instructions for visualizing ultrasound data showing an object during an interventional procedure that includes an object-influence phase during which the object is influenced at a location on the object by applying energy to the object by using an energy application element, a pre-object-influence phase preceding the object-influence phase in time and a post-object-influence phase after the object-influence phase in time, wherein the instructions, when executed by a computer, configure the computer to perform the following steps:

providing a temporally dependent ultrasound image of the object by an ultrasound image providing unit;

automatically identifying and extracting a constant reference M-mode image of the object based on a part of the temporally dependent ultrasound image, wherein the constant reference M-mode image corresponds to a reference time interval in a prior phase of the interventional procedure which precedes a current phase of the interventional procedure;

determining and updating a current M-mode image of the object based on a part of the temporally dependent ultrasound image, which corresponds to a current time interval in the current phase, wherein the current time interval is less than the duration of the current phase, wherein said updating comprises updating the current M-mode image in wrapping fashion, comprising:

adding newly acquired A-lines to the current M-mode image until the current M-mode image includes a maximum number of A-lines, and in response to the current M-mode image being updated to include the maximum number of A-lines, replace previously acquired A-lines of the current M-mode image, and not the reference image, with newly acquired replacement A-lines; and simultaneously displaying on a display, (i) the constant reference M-mode image and (ii) the current M-mode image while said updating in the wrapping fashion.

19. The non-transitory computer-readable medium of claim 18 wherein either:

(a) the current phase of the interventional procedure is the object-influence phase and the prior phase of the interventional procedure is the pre-object-influence phase; or (b) the current phase of the interventional procedure is the post-object-influence phase and the prior phase of the interventional procedure is the object-influence phase.

* * * * *